United States Patent [19]
Billings et al.

[11] Patent Number: 5,860,976
[45] Date of Patent: Jan. 19, 1999

[54] ELECTROSURGICAL CUTTING DEVICE

[75] Inventors: R. Gail Billings, Holladay; Ben D. Shirley, Salt Lake City, both of Utah

[73] Assignee: Utah Medical Products, Inc., Midvale, Utah

[21] Appl. No.: 804,320

[22] Filed: Feb. 21, 1997

Related U.S. Application Data

[63] Continuation-in-part of Ser. No. 593,618, Jan. 30, 1996.

[51] Int. Cl.$^6$ ..................................................... A61B 17/36
[52] U.S. Cl. .............................................. 606/45; 606/41
[58] Field of Search .............................. 606/32, 41–50; 607/116, 119, 122; 128/898

[56] References Cited

U.S. PATENT DOCUMENTS

| | | | |
|---|---|---|---|
| 3,987,795 | 10/1976 | Morrison | 128/303.14 |
| 4,161,950 | 7/1979 | Doss et al. | 128/303.14 |
| 4,198,957 | 4/1980 | Cage et al. | 128/1 R |
| 4,485,810 | 12/1984 | Beard | 128/303.1 |
| 4,549,073 | 10/1985 | Tamura et al. | 219/497 |
| 4,589,411 | 5/1986 | Friedman | 606/45 |
| 4,622,966 | 11/1986 | Beard | 128/303.14 |
| 5,013,312 | 5/1991 | Parins et al. | 606/37 |
| 5,171,311 | 12/1992 | Rydell et al. | 606/48 |
| 5,221,281 | 6/1993 | Klicek | 606/45 |
| 5,308,311 | 5/1994 | Eggers et al. | 606/28 |
| 5,352,868 | 10/1994 | Denen et al. | 219/501 |
| 5,360,428 | 11/1994 | Hutchinson, Jr. | 606/45 |
| 5,376,089 | 12/1994 | Smith | 606/42 |
| 5,437,665 | 8/1995 | Munro | 606/47 |
| 5,441,499 | 8/1995 | Fritsch | 606/45 |
| 5,472,442 | 12/1995 | Klicek | 606/42 |
| 5,562,503 | 10/1996 | Ellman et al. | 439/638 |
| 5,702,387 | 12/1997 | Arts et al. | 606/45 |

*Primary Examiner*—Jack W. Lavinder
*Assistant Examiner*—David M. Ruddy
*Attorney, Agent, or Firm*—Madson & Metcalf, P.C.

[57] ABSTRACT

An improved electrosurgical cutting device for connection to an electrosurgical generator has a non-conductive support member with a peripheral edge and a conducting member, distinct from the support member, disposed along at least a portion of the peripheral edge of the support member. The support member extends from a bendable shaft which may be manipulated to create an angled device. The conducting member is in electrical communication with an electrosurgical generator suitable for transmitting sufficient high frequency electrical energy to the conducting member, thereby enabling the conducting member to function as the active outlet in a monopolar circuit. The support member has a configuration that facilitates the manipulation of body tissue either with or without the presence of electrical energy at the conducting member.

28 Claims, 3 Drawing Sheets

ELECTROSURGICAL CUTTING DEVICE

RELATED APPLICATIONS

This application is a continuation-in-part of U.S. patent application Ser. No. 08/593,618, filed Jan. 30, 1996 and entitled "Electrosurgical Cutting Device" which is incorporated herein by this reference.

BACKGROUND OF THE INVENTION

1. Field of the Invention

This invention relates to electrosurgical electrode instruments for surgical cutting of body tissue.

2. Technical Background

Electrosurgical instruments are used extensively in surgical practice and the advantages of their use over conventional non-electrical surgical instruments are well recognized in the practice. Electrosurgical instruments are effective for both cauterizing and cutting body tissue. To effect cutting of body tissue the electrode is typically a thin electrode with a small contact area. Such electrosurgical instruments have been applied in both monopolar and bipolar circuits.

A monopolar circuit is composed of an electrosurgical generator with two outlet connections: an active and a dispersive connection. The dispersive connection connects to a dispersive pad which is attached to a patient's body. The dispersive pad covers sufficient contact area with the patient's body to prevent concentration of electrical energy which would harm the body tissue. The active connection is connected to an electrode which is then placed in proximity to or in contact with the body. An electrosurgical generator transmits high frequency electrical energy through the patient's body by means of the active and dispersive connections. The electrical energy present in the body is concentrated to those specific areas in proximity to the active electrode. Those cells of the body thus exposed to the concentrated electrical energy are ruptured due to pressure caused by internal heating by the concentrated current flowing from the electrode to the cells. In this manner, cutting of tissue, accompanied by cauterization is achieved.

The shape and size of the electrode may vary depending on the purpose of the surgery. Thin, wire electrodes are commonly used electrosurgical instruments. Typically, the wire electrodes are configured into needle or loop shapes. Both the needle and the loop electrodes are efficient cutters because their thinness concentrates the electrical energy to a very limited region of body tissue, thus fully utilizing the energy in the cutting process. Thin wire and loop electrode also prevent unnecessary tissue exposure to the electrical energy where cutting or burning of tissue is not desired.

Wire electrodes are limited in their cutting performance due to their lack of mechanical rigidity and their general fragile nature. This is especially true when the electrodes become hot during the surgical cutting process. Furthermore, it is often desirable for the surgeon to use the cutting electrode, without current applied, as a mechanical tool to separate tissues (i.e., cold or mechanical dissection) that are adjacent to each other but which should not be exposed to the electrical energy of electrosurgical cutting. Naturally, the thin electrodes function poorly in mechanically separating body tissue because they lack sufficient mechanical reinforcement to effect proper dissection.

An electrosurgical instrument that is conveniently used both for electrosurgical cutting and mechanical dissection is the paddle electrode. This elongated, flat electrode has the mechanical strength to allow mechanical dissection and is able to create sufficient current concentration on its edges to accomplish good electrosurgical cutting. However, compared to a needle or wire loop electrode, the paddle electrode is a less efficient cutter because much of the high frequency electrical energy supplied by the electrosurgical generator flows to the body tissue through the sides of the paddle electrode where no exposure or cutting activity is desired. In some circumstances, the current flowing through the sides of the paddle electrode may have a beneficial effect in cauterizing the wound created in cutting through the tissue. However, in most cases, it is a wasteful use of current resulting in an extra burden for the electrosurgical generator and requires a larger power setting of the generator to accomplish the cut. Using a paddle electrode also frequently results in thermal injury to the tissue along the cut and in troublesome sticking of tissue to the sides of the paddle. Nevertheless, the paddle electrode has the advantages of superior mechanical strength and a flat shape that acts as a rudder giving the surgeon a better ability to guide the electrode along a straight or smooth curved line.

One attempt to solve the side conduction problem of the paddle electrode has been to coat the sides of the paddle with plastic, typically TEFLON, which diminishes the current conducted out the side and prevents sticking of the tissue to the paddle electrode. This solution is only partially successful because at the high frequencies used for electrosurgery, there is substantial current that is capacitively coupled from the metal of the paddle, through the plastic coating, and to the body tissue. Thus, a more successful and permanent solution has yet to be realized.

From the foregoing, it will be appreciated that it would be an advancement in the art to provide an improved electrosurgical cutting device which realizes the advantages of the wire electrode and paddle electrode while at the same time eliminating their disadvantages. Specifically, it would be an advancement in the art to provide an electrosurgical cutting device which concentrates the electrical energy to a limited area of body tissue, yet has sufficient mechanical rigidity to allow improved cutting performance and to permit mechanical dissection. Yet another advancement in the art is to provide a device with the above features which is simple and economical to manufacture.

Such an electrosurgical cutting device is disclosed and claimed herein.

BRIEF SUMMARY OF THE INVENTION

The present invention provides an electrosurgical cutting device to be used generally in all areas of surgical cutting. The present invention particularly contemplates the use of the electrosurgical cutting device as the active outlet in a monopolar circuit. The present invention is designed to efficiently cut body tissue through the process of cell lysis using heat produced by electrical current concentrated at the site where cutting is desired. In the absence of electrical energy, the device is capable of manipulating or mechanically dissecting body tissue. Compared to conventional paddle electrodes, cutting efficiency is improved by greater concentration of current in the tissues. Tissue thermal damage is reduced by elimination of current dispersed away from the cutting edge.

The invention comprises a conducting member along the outer perimeter of a non-conductive support member. In the preferred embodiment the conducting member comprises a thin, wire electrode which is connected to a source of high frequency electrical energy. The non-conductive support member gives the wire electrode additional support, strength, and rigidity. The rigidity provided by the non-conducting support member provides the surgeon better control in positioning and guiding the device along a precise cutting path. Furthermore, with the electrical energy to the conducting member turned off, the support member possesses sufficient mechanical strength to manipulate or mechanically dissect body tissue.

The support member is generally of a shape and length suitable to cutting body tissue. The support member preferably has a peripheral edge that is sufficiently thin to allow efficient cutting, but thick enough to ensure sufficient strength in the support member. The support member is preferably composed of a rigid, thermally stable, non-conductive material. The support member should retain its strength and utility when exposed to the heat produced by electrical energy passing through the supported conducting member and the adjacent tissue. Because, the support member does not conduct electrical energy, electrical energy is conducted only along the peripheral edge where the conducting member is disposed. Consequently, electrical energy is only applied where the conducting member comes into contact with the body tissue. In a preferred embodiment, the support member is composed of any of a variety of ceramic substrates or plastics commonly known in the art but can be made of any other suitable rigid, non-conductive material.

The invention further comprises a bendable shaft which is attached to the support member. The bendable shaft allows the surgeon to manipulate the shaft as desired to create an angled instrument to facilitate cutting. In a preferred embodiment, the bendable shaft is made of a conductive material and is in electrical communication with the conducting member thereby providing the electrical energy to the conducting member. The shaft extends from either a handle or an adaptable connector. The adaptable connector would be a type which inserts into a surgical electrode handle.

The conducting member may be disposed along a portion of or along the entire exposed peripheral edge of the support member. Those skilled in the art will recognize that many design configurations are possible by altering the shape of the support member and the placement of the conducting member along at least a portion of the peripheral edge of the support member. Although such configurations may result in different methods of handling the device due to different shapes and different points of contact of electrical energy, such variations are within the scope of the claimed invention.

Electrical connection between the conducting member and an electrosurgical generator is made using conventional connecting wire or any other suitable means. The connecting wire is of a type suitable for the conduction of high frequency electrical current, and is preferably insulated. The electrosurgical generator is of a type commonly used in the industry for transmitting high frequency electrical energy during electrosurgical operations.

In the course of operation, the electrosurgical generator produces a high frequency energy which is transmitted through the connecting wire to the conducting member. The surgeon then guides the conducting member to the specified area of body tissue where the incision is to occur.

Thus, it is an object of the invention to provide an electrosurgical cutting device which concentrates electrical energy to a specified area of body tissue and reduces unnecessary thermal exposure.

It is a further object of the invention to provide an electrosurgical cutting device with sufficient mechanical strength to manipulate body tissue.

It is also an object of the invention to provide an electrosurgical cutting device which can be manually manipulated to create an angled device.

These advantages of the present invention will become more fully apparent by examination of the following description of the preferred embodiments and the accompanying drawings.

BRIEF DESCRIPTION OF THE DRAWINGS

To better understand the invention, a more particular description of the invention will be rendered by reference to the appended drawings. These drawings only provide information concerning typical embodiments of the invention and are not to be considered limiting of its scope. The invention will be described and explained with additional specificity and detail through the use of the accompanying drawings, in which.

DESCRIPTION OF THE PREFERRED EMBODIMENT

Figure 1:
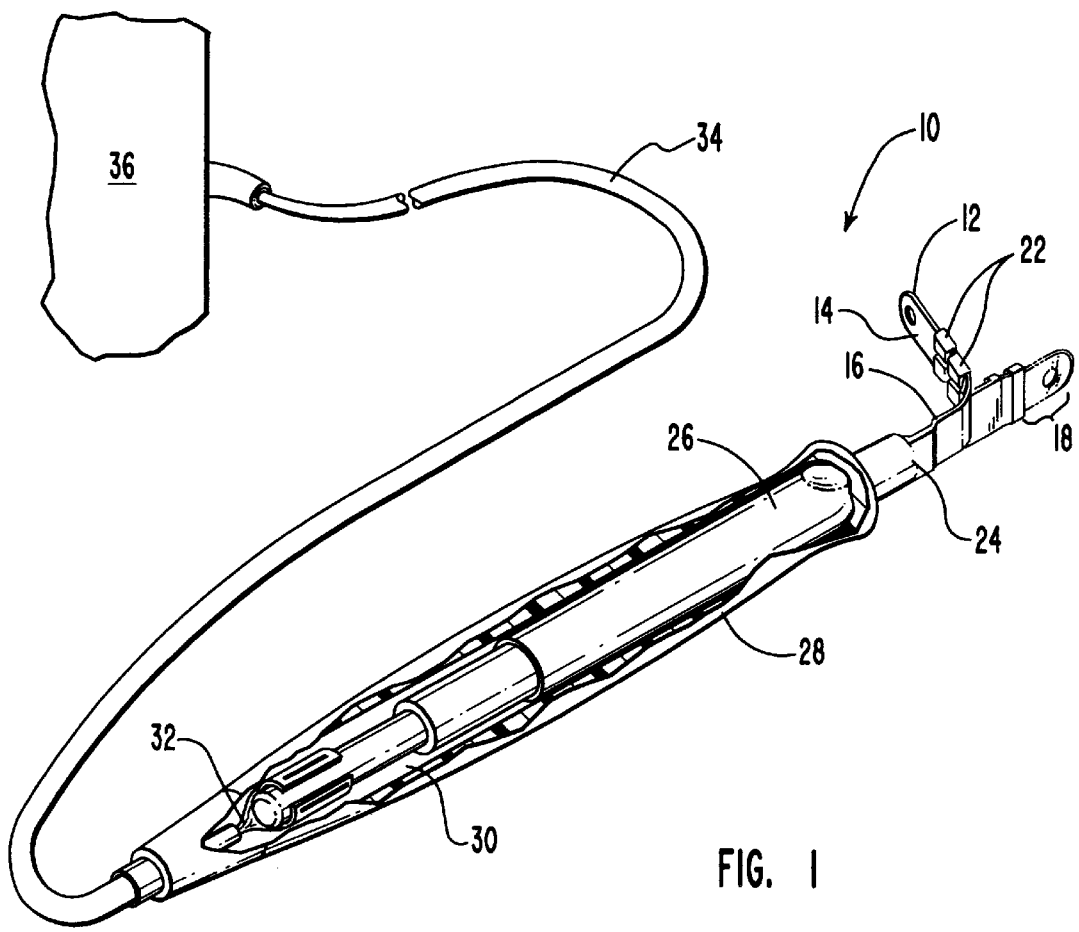
FIG. 1 is a perspective view of one embodiment of the electrosurgical cutting device of the present invention.
Figure 2:
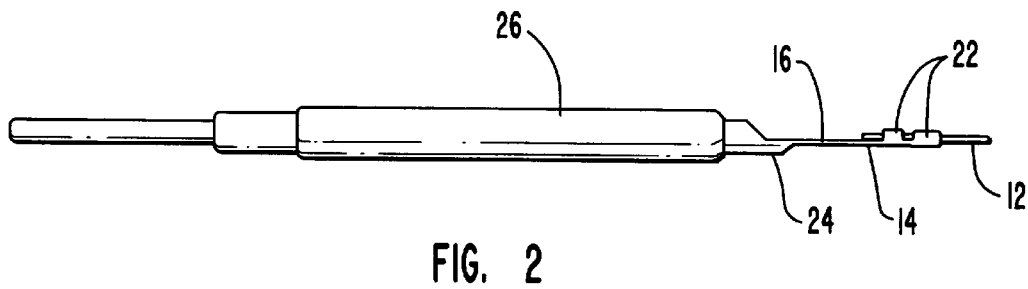
FIG. 2 is a side view illustrating one embodiment of the electrosurgical cutting device of the present invention.
Figure 3:
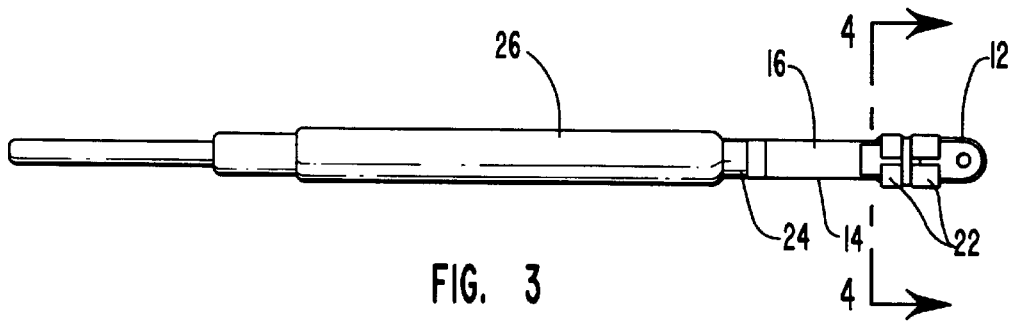
FIG. 3 is a side view of one embodiment of the electrosurgical cutting device of the present invention showing the obverse, or reverse surface area of the support member and the bendable shaft.

Reference is now made to the figures wherein like parts are referred to by like numerals throughout. With reference to FIGS. 1, 2, and 3, there is illustrated an electrosurgical cutting device 10 of the present invention. The cutting device 10 may be used as the active outlet of a monopolar circuit. The cutting device 10 comprises a conducting member 12, a support member 14 made of a non-conductive material, and a bendable shaft 16.

The support member 14 is made of a thermally stable material so that the support member 14 will be unaffected by the heat produced by electrical energy passing through the conducting member 12. The material is preferably from any one of a variety of ceramic substrates commonly known and used in the art, but the support member 14 can be made of any other suitable material such as heat resistant plastic.

Figure 4:
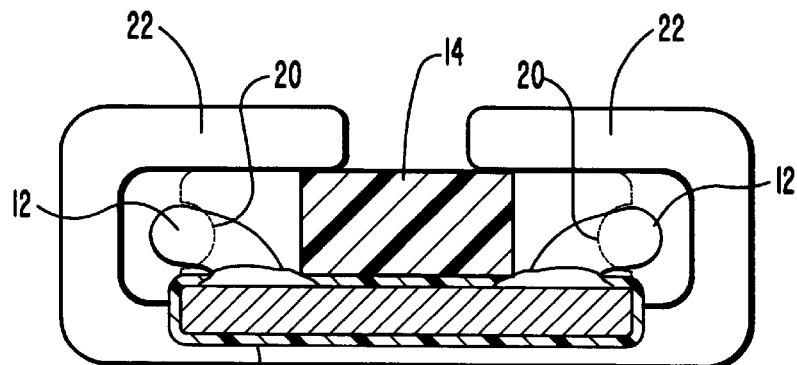
FIG. 4 is an enlarged sectional view of the support member along line 4—4 of FIG. 3.
Figure 7:
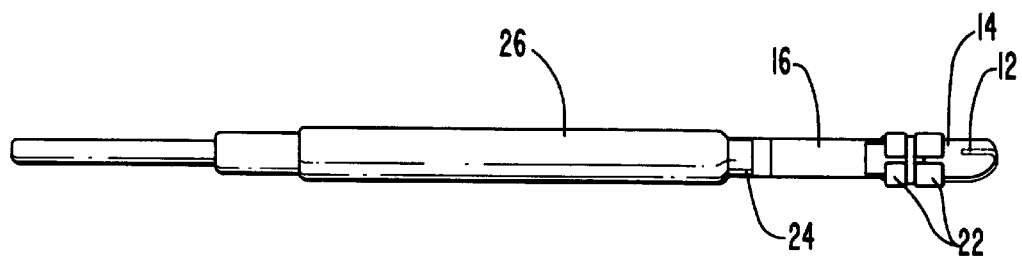
FIG. 7 is a side view of an embodiment of an electrosurgical cutting device with a portion of the conducting member (shown in phantom lines) passing internally through the support member.
Figure 8:
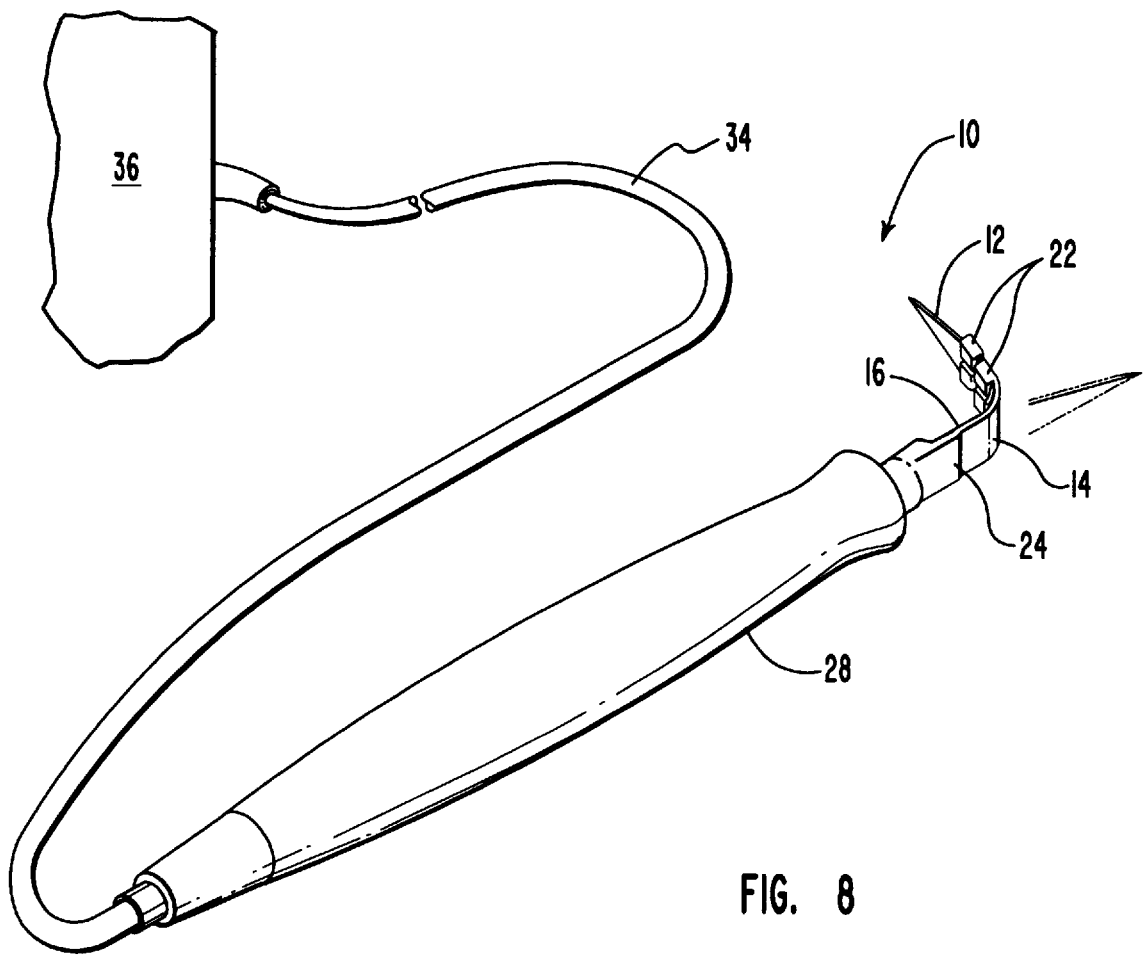
FIG. 8 is a perspective view of an embodiment of an electrosurgical cutting device with the bendable shaft extending from the handle.

The support member 14 may be configured in various shapes suitable for cutting body tissue, including paddle shapes similar to conventional paddle electrodes with an obverse side, reverse side, width dimension, and a peripheral edge 18. Optionally, the support member 14 may also be configured in a variety of knife blade or scalpel shapes such as shown in FIGS. 7 and 8. The support member 14 is configured with a thin peripheral edge 18 with the conducting member 12 disposed thereon, yet has sufficient mechanical strength to permit cold or mechanical dissection, separating and manipulating the body tissue without conduction of electrical energy. There is sufficient space on the peripheral edge 18 to receive the conducting member 12. Alternatively, the support member 14 may be formed with a groove 20 along the peripheral edge 18 in which the conducting member 12 is securely seated as shown in FIG. 4.

The conducting member 12 is preferably embodied as a wire electrode and primary consideration is given to this embodiment in the specification. However, it is understood, and those skilled in the art will appreciate, that other embodiments of the conducting member 12 such as conductive materials in the form of deposits, etchings, or sprays would be included within the scope of the present invention.

In the presently preferred embodiment, the conducting member 12 is separate and distinct from the support member 14 and is composed of a material which is suitable to conduct high frequency electrical energy for cutting body tissue. In one preferred embodiment, the conducting member 12 is composed of tungsten or stainless steel. The conducting member 12 is secured to the peripheral edge 18 of the support member 14, such that the surgeon can easily guide the conducting member 12 to the position of desired contact with the body tissue.

Figure 5:
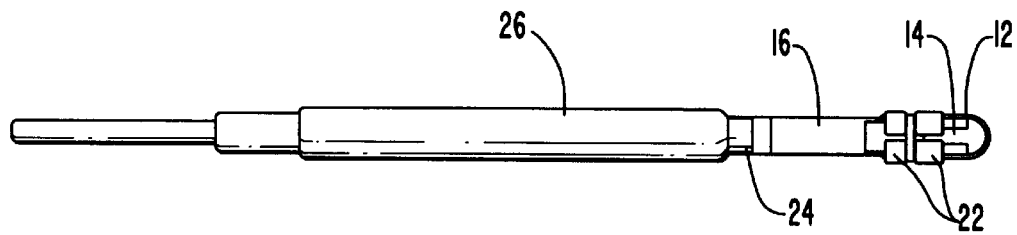
FIGS. 5 and 6 are side views of alternative embodiments of the electrosurgical cutting device with the conducting member encompassing additional fill material other than the support member.
Figure 6:
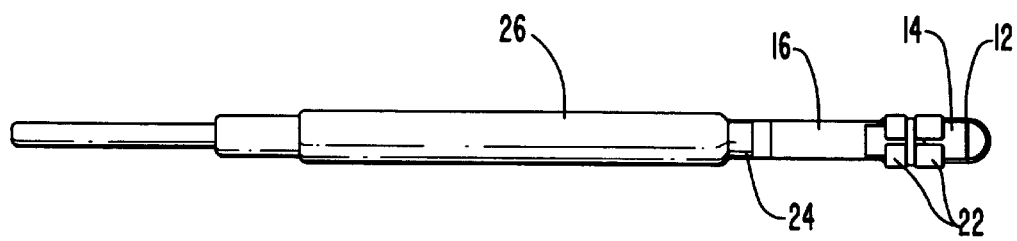

In the embodiment depicted in FIGS. 1–3, the conducting member 12 is embodied as a wire loop electrode with a wire forming a loop around the support member 14. The conducting member 12 is preferably disposed along the entire exposed peripheral edge 18. However, those skilled in the art will recognize that a variety of alternative configurations and embodiments are possible. For example, as shown in FIGS. 5 and 6, the loop formed by the conducting member 12 may encompass the support member 14 as well as some other fill material 15, such as air. The conducting member 12 may only be partially disposed along the peripheral edge 16, see FIGS. 7 and 8. In FIG. 7 the conducting member 12 is partially disposed along the peripheral edge 18 and a portion of the conducting member 12 is internal to the support member 14. In FIG. 8, the support member 14 is embodied in a scalpel shape and the conducting member 12 is disposed only along the leading edge of the support member 14. These configurations are illustrative of a variety of embodiments which are possible without departing from the scope of the invention.

The support member 14 extends from the bendable shaft 16. In the preferred embodiment, the bendable shaft 16 is configured with lugs 22 on its distal end. The support member 14 is secured within the lugs 22. Alternative methods of securing the bendable shaft 16 to the support member 14, such as screws or adhesives, are well known in the art and are within the scope of the invention. The bendable shaft 16 is flexible to allow manual manipulation by the surgeon to create an angled instrument. The bendable shaft 16 is bent to a desired angle which will facilitate cutting of body tissue in difficult to reach locations. FIG. 1 illustrates the invention as it would appear with the bendable shaft 16 bent to a desired angle.

The bendable shaft 16 is thin enough to allow bending by human hands yet generally retains the bent angle during the normal course of surgical procedure. In a preferred embodiment, the bendable shaft 16 is made of a conductive material such as stainless steel or any number of various metals. Such material is flexible and has sufficient mechanical strength to retain a desired angle. The conducting member 12 is placed in electrical communication with the conductive, bendable shaft 16 as shown in FIG. 4. This allows the conductive, bendable shaft 16 to deliver high frequency electrical energy to the conducting member 12. In this embodiment, the bendable shaft 16 is covered with a non-conductive coating 24 such as a plastic overmold. The non-conductive coating 24 prevents undesired conduction of electrical energy from the bendable shaft 16.

In an alternative embodiment, the bendable shaft 16 does not conduct high frequency electrical energy. Rather, the high frequency electrical energy is delivered to the conducting member 12 by other means such as a wire connection directly to the conducting member 12. In such an embodiment a non-conductive coating 24 would obviously not be necessary.

FIGS. 1 through 7 show the preferred embodiment of the invention in which the bendable shaft 16 extends from the distal end of an adaptable connector 26. The adaptable connector 26 is a standard configuration known in the industry. The adaptable connector 26 engages a source of electrical energy for the conducting member 12. As used in the present invention, the adaptable connector 26 also permits attachment of the bendable shaft 16, support member 14, and conducting member 12 to a handle 28 to facilitate hand-held manipulation of the cutting device 10.

FIG. 1 shows the engagement of the proximal end of the adaptable connector 26 into the interior cavity 30 of the handle 28. The handle 28 receives the adaptable connector 26 in a mechanical engagement and enables transmission of electrical energy through a connecting wire 32. The connecting wire 32 is insulated and capable of carrying high frequency electrical energy to the conducting member 12 through the adaptable connector 26. The connecting wire 32 exits out the proximal end of the handle 28 where it is enclosed within a cable 34 suitable for protecting the connecting wire 32. The connecting wire 32 is connected to the output of an electrosurgical generator 36.

FIG. 8 is an alternative embodiment showing the bendable shaft 16 attached directly to a handle 28, thereby eliminating the adaptable connector. In such an embodiment, the handle 28 delivers electrical energy to the conducting member 12 through a connecting wire 32 which travels along the longitudinal axis of the handle 28. As in FIG. 1, the connecting wire 32 is enclosed within a cable 34 as it exits the handle 28 and connects to the output of an electrosurgical generator 36.

The electrosurgical generator 36 is of a type commonly known and used in the industry for providing an adjustable output of high frequency electrical energy. By controlling the output of the electrosurgical generator 36, the operator or surgeon is able to transmit sufficient high frequency electrical energy to the conducting member 12 to enable the conducting member 12 to cut the desired body tissue.

It should be appreciated that the apparatus of the present invention is capable of being incorporated in the form of a variety of embodiments, only a few of which have been illustrated and described above. The invention may be embodied in other forms without departing from its spirit or essential characteristics. For instance, the connecting wire 18 may enter from the midsection of the handle 28 rather than from the proximal end or even connect directly to the conducting member 12.

The improved electrosurgical cutting device provides greater mechanical strength due to the support member 14 which provides superior cutting and manipulation of body tissue. At the same time, the electrosurgical cutting device continues to concentrate electrical energy and reduce unnecessary thermal exposure. The incorporation of a bendable shaft 16 allows the surgeon to angle the instrument as desired to reach areas of body tissue.

The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed is:

1. An electrosurgical cutting device for communicating electrically with an electrosurgical generator for use in a monopolar circuit comprising:

a generally flat non-conductive support member having a peripheral edge;

a bendable shaft connected to said non-conductive support member, wherein said shaft is bendable by manual manipulation to a desired angle; and a conducting member, distinct from said support member, configured to function as an active outlet in a monopolar circuit for electrosurgical cutting and disposed along at least a portion of the peripheral edge of said support member, said conducting member configured to be in electrical communication with only one pole of the electrosurgical generator to receive high frequency electrical energy from the electrosurgical generator.

2. The electrosurgical cutting device of claim 1 wherein said conducting member comprises a wire electrode.

3. The electrosurgical cutting device of claim 2 wherein said wire electrode comprises a tungsten wire.

4. The electrosurgical cutting device of claim 2 wherein said wire electrode comprises a stainless steel wire.

5. The electrosurgical cutting device of claim 1 wherein said conducting member forms a wire loop electrode with said support member filling the center of the loop.

6. The electrosurgical cutting device of claim 1 wherein a portion of said conducting member is internal to said support member.

7. The electrosurgical cutting device of claim 1 wherein said support member is composed of a thermally stable material.

8. The electrosurgical cutting device of claim 1 wherein said support member is shaped in the form of a paddle with an obverse side, a reverse side, and the peripheral edge.

9. The electrosurgical cutting device of claim 1 wherein said support member is composed of ceramic material.

10. The electrosurgical cutting device as in claim 1 wherein said support member is configured to allow the manipulation of body tissue in the absence of electrical energy to said conducting member.

11. The electrosurgical cutting device of claim 1 wherein said support member is configured with a groove along at least a portion of the peripheral edge of said support member and said conducting member is seated in the groove.

12. The electrosurgical cutting device of claim 1 wherein said bendable shaft is comprised of a conductive material and is in electrical communication with said conducting member.

13. An electrosurgical cutting device for communicating electrically with an electrosurgical generator for use in a monopolar circuit comprising:

a non-conductive support member having a peripheral edge;

a bendable, conductive shaft formed of a unitary member and connected to said non-conductive support member, wherein said shaft is bendable by manual manipulation to a desired angle;

a conducting member, distinct from said support member, configured to function as an active outlet in a monopolar circuit for electrosurgical cutting and disposed along at least a portion of the peripheral edge of said support member and in electrical communication with said shaft, said conducting member configured to be in electrical communication with only one pole of the electrosurgical generator to receive high frequency electrical energy from the electrosurgical generator; and an adaptable connector in electrical communication with said shaft, said adaptable connector having a proximal and distal end, said shaft extending from the distal end of said adaptable connector.

14. The electrosurgical device of claim 13 further comprising a handle configured to receive in electrical and mechanical engagement the proximal end of said adaptable connector.

15. The electrosurgical device of claim 13 further comprising a connecting wire which passes through the interior of said handle and allows said adaptable connector to electronically communicate with the electrosurgical generator, thereby allowing the electrosurgical generator to transmit high frequency electrical energy through said adaptable connector and said shaft to said conducting member to enable said conducting member to cut body tissue.

16. The electrosurgical device of claim 13 wherein said support member is composed of thermally stable material.

17. The electrosurgical device of claim 13 wherein said support member is configured to allow the manipulation of body tissue in the absence of electrical energy to said conducting member.

18. The electrosurgical device of claim 13 wherein said support member is configured with a groove along at least a portion of the peripheral edge of said support member and said conducting member is seated in the groove.

19. The electrosurgical cutting device of claim 13 wherein a portion of said conducting member is internal to said support member.

20. The electrosurgical cutting device of claim 13 wherein said conducting member comprises a wire electrode.

21. The electrosurgical cutting device of claim 13 wherein at least a portion of said shaft is enclosed within an insulative coating.

22. An electrosurgical cutting device for communicating electrically with an electrosurgical generator for use in a monopolar circuit comprising:

a handle having a proximal end and a distal end;

a bendable, conductive shaft formed of a unitary member and extending from the distal end of said handle, wherein said shaft is bendable by manual manipulation to a desired angle;

a non-conductive, thermally stable support member extending from said shaft, said support member having a peripheral edge, said support member being configured to allow the manipulation of body tissue;

a conducting member, distinct from said support member, configured to function as an active outlet in a monopolar circuit for electrosurgical cutting and disposed along at least a portion of the peripheral edge of said support member, said conducting member electrically communicating with said shaft, said shaft configured to be electrically communicating with only one pole of the electrosurgical generator to receive high frequency electrical energy from the electrosurgical generator.

23. The electrosurgical device of claim 22 further comprising a connecting wire which constitutes the means by which said electrosurgical generator electrically communicates with said shaft.

24. The electrosurgical device of claim 22 wherein said support member is configured with a groove along at least a portion of the peripheral edge of said support member and said conducting member is seated in the groove.

25. The electrosurgical device of claim 22 wherein said conducting member comprises a wire electrode.

26. The electrosurgical device of claim 22 wherein at least a portion of said shaft is enclosed within an insulative coating.

27. A method for electrosurgically cutting body tissue comprising the steps of:
   disposing a conducting member configured to function as an active outlet in a monopolar circuit for electrosurgical cutting along at least a portion of a peripheral edge of a non-conductive, thermally stable support member;
   connecting said support member to a bendable, conductive shaft formed of a unitary member wherein said shaft is bendable by manual manipulation to a desired angle and generally retains the desired angle during operation;
   placing said conducting member in electrical communication with said shaft and in electrical communication with only one pole of the electrosurgical generator to receive high frequency electrical energy from the electrosurgical generator;
   placing a dispersive pad in electrical communication with an opposing pole of the electrosurgical generator and in contact with body tissue to thereby allow the dispersive pad to function as a dispersive connection in a monopolar circuit; and
   positioning said conducting member adjacent to the body tissue to complete the monopolar circuit and to transmit high frequency electrical energy from the electrosurgical generator through the shaft and to the conducting member to thereby cut body tissue.

28. The method of claim 27 further comprising the step of enclosing at least a portion of said shaft in an insulative coating.

* * * * *